US008180019B2

(12) United States Patent
Bertozzi et al.

(10) Patent No.: US 8,180,019 B2
(45) Date of Patent: May 15, 2012

(54) METHODS AND SYSTEMS FOR COMPUTER TOMOGRAPHY OF NUCLEAR ISOTOPES USING NUCLEAR RESONANCE FLUORESCENCE

(75) Inventors: William Bertozzi, Lexington, MA (US); Robert J. Ledoux, Harvard, MA (US)

(73) Assignee: Passport Systems, Inc., Billerica, MA (US)

( * ) Notice: Subject to any disclaimer, the term of this patent is extended or adjusted under 35 U.S.C. 154(b) by 0 days.

(21) Appl. No.: 12/958,006

(22) Filed: Dec. 1, 2010

(65) Prior Publication Data
US 2011/0164732 A1    Jul. 7, 2011

Related U.S. Application Data

(63) Continuation of application No. 11/511,182, filed on Aug. 28, 2006, which is a continuation of application No. 10/994,115, filed on Nov. 19, 2004, now Pat. No. 7,120,226, application No. 12/958,006, which is a continuation-in-part of application No. 12/344,880, filed on Dec. 29, 2008, now abandoned.

(60) Provisional application No. 60/524,551, filed on Nov. 24, 2003, provisional application No. 61/016,946, filed on Dec. 27, 2007.

(51) Int. Cl.
*G01N 23/04* (2006.01)
*G01N 23/223* (2006.01)
*G21K 1/10* (2006.01)
*H05G 1/60* (2006.01)
*G01B 15/00* (2006.01)

(52) U.S. Cl. ............... 378/57; 378/21; 378/23; 378/46; 378/90

(58) Field of Classification Search ........... 378/4–6, 378/21, 23–25, 44–46, 49, 51, 57, 62, 70, 378/71, 76, 82, 86, 87, 90
See application file for complete search history.

(56) References Cited

U.S. PATENT DOCUMENTS

| | | | |
|---|---|---|---|
| 3,496,357 A * | 2/1970 | Weinzierl et al. | 376/159 |
| 4,446,568 A | 5/1984 | Williams et al. | |
| 4,788,704 A | 11/1988 | Donges et al. | |
| 4,941,162 A | 7/1990 | Vartsky et al. | |
| 5,115,459 A | 5/1992 | Bertozzi | |

(Continued)

FOREIGN PATENT DOCUMENTS
JP    57-058625 A    4/1982
(Continued)

OTHER PUBLICATIONS

Degener et al., Depole Excitations in [48] Ti Studied by Nuclear Resonance Fluorescense, Nuclear Physic A513 (1990) 29-42.

(Continued)

*Primary Examiner* — Anastasia Midkiff
(74) *Attorney, Agent, or Firm* — Foley Hoag LLP

(57) ABSTRACT

The transmission of photons through a target produces "holes" in the transmitted energy spectrum that are characteristic of the NRF energies of the nuclear isotopes in the target. Measuring the absorption via the transmission of these photons through a target allows the production of tomographic images that are associated with specific nuclear isotopes. Thus three-dimensional density patterns are generated for the elements in a container. The process is very much like standard X-ray tomography but it identifies specific nuclear isotopes as well as their densities.

60 Claims, 4 Drawing Sheets

U.S. PATENT DOCUMENTS

| | | | |
|---|---|---|---|
| 5,247,177 | A | 9/1993 | Goldberg et al. |
| 5,323,004 | A * | 6/1994 | Ettinger et al. ............ 250/336.1 |
| 5,420,905 | A * | 5/1995 | Bertozzi ........................ 378/88 |
| 5,600,303 | A * | 2/1997 | Husseiny et al. .......... 340/568.1 |
| 5,600,700 | A | 2/1997 | Krug et al. |
| 5,642,393 | A | 6/1997 | Krug et al. |
| 6,018,562 | A | 1/2000 | Willson |
| 6,088,423 | A | 7/2000 | Krug et al. |
| 6,108,396 | A | 8/2000 | Bechwati et al. |
| 6,175,609 | B1 | 1/2001 | Edic et al. |
| 6,345,113 | B1 | 2/2002 | Crawford et al. |
| 6,442,233 | B1 | 8/2002 | Grodzins et al. |
| 7,430,479 | B1 * | 9/2008 | Holslin et al. ................. 702/22 |
| 2004/0109532 | A1 | 6/2004 | Ford et al. |
| 2005/0094765 | A1 | 5/2005 | Bijani et al. |
| 2005/0111619 | A1 | 5/2005 | Bijjani et al. |

FOREIGN PATENT DOCUMENTS

| | | |
|---|---|---|
| JP | 05-100049 A | 4/1993 |
| JP | 3425600 T | 4/1997 |
| JP | 09-127021 A | 5/1997 |
| JP | 2002-243671 A | 8/2002 |
| WO | WO-9939189 | 8/1999 |

OTHER PUBLICATIONS

Metzger, Electric Dipole Transitions from the 2.6 MeV septuplet in Bi209, Physical Review 187 (1969) 1680-1682.

International Search Report, Int'l App. No. PCT/US2004/039043.

Written Opinion of the International Searching Authority, Int'l App. No. PCT/US2004/039043.

Bertozzi, William, Poster: Material Identification and Object Imaging using Nuclear Resonance Fluorescense, Jul. 18, 2003, MIT, Dept. of Energy's Ofc of Nuclear Physics Workshop on the Role of the Nuclear Physics Research Community in Combating Terrorism. (previously provided with U.S. Appl. No. 11/511,882).

Office Action mailed Nov. 16, 2010 in Japanese Patent Application No. 2006-541575.

Office Action mailed Jun. 28, 2011 in Japanese Patent Application No. 2006-541575.

* cited by examiner

METHODS AND SYSTEMS FOR COMPUTER TOMOGRAPHY OF NUCLEAR ISOTOPES USING NUCLEAR RESONANCE FLUORESCENCE

CROSS-REFERENCE TO RELATED APPLICATION

This application is a continuation-in-part of U.S. patent application Ser. No. 11/511,182, filed on Aug. 28, 2006, which is a continuation of U.S. patent application Ser. No. 10/994,115, filed on Nov. 19, 2004, and is now U.S. Pat. No. 7,120,226, which claims the benefit of U.S. Provisional Application No. 60/524,551, filed on Nov. 24, 2003; this application is also a continuation-in-part of U.S. patent application Ser. No. 12/344,880, filed on Dec. 29, 2008, which claims the benefit of U.S. Provisional Patent Application No. 61/016,946, filed on Dec. 27, 2007. All aforementioned applications are hereby incorporated herein by reference.

FIELD

This disclosure relates to the use of Nuclear Resonance Florescence (NRF) to construct a three-dimensional image showing the presence of a specific nuclear isotope in an object by means of tomographic reconstruction.

BACKGROUND

Tomographic reconstruction has been employed in conjunction with measurements of x-ray absorption to generate three-dimensional images of objects, and has been of great value in medical and other types of imaging. It has been effectively employed to image differences in density based on the stopping power of the imaged objects for the x-rays employed. Unfortunately, conventional tomographic reconstruction employed heretofore, while able to produce high-quality imaging, has not been able to produce images that reliably distinguish between different elements or isotopes.

Nuclear Resonance Fluorescence (NRF) results when a nuclear isotope is resonantly excited by photon absorption and then subsequently decays via photon emission to a lower-lying state of that nucleus. The energies of the incident photons that are resonant with a specific isotope are determined by the structure of that specific isotope and the nature of the strong nuclear interactions that bind its nucleus. These excitation energies are unique for each nuclear isotope and present a signature that identifies the presence of that specific nuclear isotope. The resulting emitted photon energies are characteristic of the specific isotope and therefore may uniquely allow the identification of the presence of that isotope in a region of space. Because the photon energies of NRF states are in the MeV energy region, the photons involved are very penetrating, allowing for deep penetration through materials.

These attributes of NRF technology enable many practical applications. For example, the isotopic detection capabilities of NRF combined with its deep penetrability make it an effective non-intrusive inspection modality for cargo containers, suitcases and packages. See U.S. Pat. No. 5,115,459, Bertozzi, "Explosives Detection Using Resonance Fluorescence of Bremsstrahlung Radiation," U.S. Pat. No. 5,420,905, Bertozzi, "Detection of Explosives and Other Materials Using Resonance Fluorescence, Resonance Absorption, and Other Electromagnetic Processes with Bremsstrahlung Radiation," and U.S. Pat. No. 7,120,226, Ledoux et al., "Adaptive Scanning Of Materials Using Nuclear Resonance Fluorescence Imaging," the contents of all of which are hereby incorporated by reference.

SUMMARY

The transmission of incident photons through a target depends in part on attenuation due to standard electromagnetic processes such as the photoelectric effect, Compton scattering, pair production, Raleigh scattering and Delbruck scattering. However, the transmission also depends on the cross section for resonant absorption by the nuclear isotopes in the path of the photon beam. By monitoring the transmission of photons with specific resonant energies and comparing that transmission to the transmission of photons at nearby energies where no nuclear resonances exist in the material, the absorptive effect of specific nuclear isotopes due to nuclear resonances can be determined. In this way a transmission image can be formed that is determined by the resonant absorption of a unique nuclear isotope. This can provide a two dimensional projection of the amount of a specific nuclear isotope in a target or container.

To detect a specific isotope uniquely, the energy resolution of the photon detection system must be narrow enough to avoid significant contamination by neighboring non-resonant photons, or the photon source must provide photons within a sufficiently narrow energy range. NRF states of nuclei that are strong enough to be useful generally are in the range of approximately 25 meV (herein meV=$10^{-3}$ eV and MeV=$10^6$ eV) or greater in width. Rarely do such nuclear isotope resonances have radiative widths much in excess of 10 eV. Thus, monochromatic photons are appropriate for such a technology to succeed. There are numerous technologies that can provide such monochromatic photons and tune their energies to be appropriate for resonance fluorescence in a variety of nuclear isotopes. These technologies are well known to those experienced in the art and will not be elaborated upon further in this disclosure except to mention a few among others such as: neutron capture, proton capture reactions such as (p,α)γ, laser back scattering and resonant scattering of photons. See U.S. Pub. Patent Application 2006/0188060A1, Bertozzi et al., "Use Of Nearly Monochromatic And Tunable Photon Sources With Nuclear Resonance Fluorescence In Non-Intrusive Inspection Of Containers For Material Detection And Imaging," incorporated herein by reference.

When the source provides photons with an energy spectrum comparable in width to or narrower than that of the NRF resonant states of a nucleus, then the transmission detector need not be of very narrow energy resolution because the incident energy can be chosen so that all the photons are sampling the nuclear resonant absorption. (In fact, broader incident energy spectra, such that they have an energy spread that is multiples of the NRF line width, may still be useful depending on the resulting signal to noise ratio achievable, and indeed the peak of the incident photon energy spectrum may deviate from the center of the resonance, so long as sufficient overlap is present; hereinafter, references to "comparable width" spectra will be understood to encompass these possibilities as well.) Then, for example, the incident energy may be changed to be non-resonant, and the difference in flux measured to determine the quantity of the isotope present along the beam path. When, on the other hand, the source provides a photon beam with an energy resolution that is very broad compared to the width of the NRF resonant state in a nucleus, the low resolution scheme for detection is severely limited by the background photons that only sample the general non-nuclear absorption processes described above. In this case the nuclear signal can be lost to the background.

However, a photon beam that has a broad distribution of photon energies can be very useful because it will allow many nuclear species to be detected since there are always photons available at any energy within the energy spectrum of the photon source. In this case the detector may have a very narrow energy resolution that is comparable to or narrower than that of the width of the NRF state of the material to be detected. (In fact, detectors with worse resolutions, such that they can only resolve energies to within multiples of the NRF line width, may still be useful depending on the resulting signal to noise ratio achievable; hereinafter, references to "comparable resolution" will be understood to encompass this possibility as well.) If detectors are available that can measure the energy of the photons scattered from or transmitted through the target with sufficient accuracy, they may be utilized. Alternatively, a reference scatterer of the same material as that to be detected may be placed in the transmitted beam beyond the target and may provide the basis of a detection scheme. A reference scatterer of the material to be detected preferentially scatters those photons that lie within the region of the NRF states of that nucleus, and a detector viewing these scattered photons will therefore measure the flux at that energy that has been transmitted through the target. Nuclei of the same species in the target container will attenuate these photons preferentially and this preferential attenuation or decreased transmission at the resonant energy will be determined by this system and attributed to the corresponding nuclear resonant absorption. See U.S. Pat. Nos. 5,115,459; 5,420,905; and 7,120,226, all cited and previously incorporated above.

A nuclear isotope may have more than one NRF state that is appropriate for the identification of that isotope. In such cases multiple NRF states may be used to identify the isotope in question and reduce any ambiguities due to accidental overlap with other isotopes. Having more than one NRF state also may improve the statistical confidence in the measurement.

In the cases discussed above, the total amount of nuclear absorption is related to the amount of material in the photon beam path by the standard expression:

$$I = I_0 e^{-\int_0^T \rho_i(x,y) \mu_i \, dx} \quad \text{(Equation 1)}$$

In Equation 1, $\rho_i(x,y)$ is the density (g/cm$^3$) of a specific nuclear isotope at the position (x,y) in the target and $\mu_i$ is the nuclear mass absorption coefficient (cm$^2$/g) for that specific nuclear isotope. The subscript, i, indicates a specific nuclear isotope. T is the thickness of the material in the x-direction. The equation relates the incident intensity, $I_0$, and the transmitted intensity, I, via the integral, over the photon path through the material, of the product of density and nuclear mass absorption coefficient. The coordinates (x,y) are within a "slice" of the material in a target; that is, x is the distance through the target along the beam path, while y is the distance in one direction off that path and x and y lie in a plane that defines the "slice". This equation therefore relates to a single "slice" of the target and treats the direction off the beam path in the direction perpendicular to y as a constant; these are distances perpendicular to the plane of the "slice" and serve to define other "slices".

The product of the nuclear mass absorption coefficient and the density of the nuclear isotope is the effective parameter in Equation 1. The mass absorption coefficient is related to the cross section for NRF absorption by the standard relation:

$$\mu = [\text{Cross Section (cm}^2\text{)}] \times [\text{Avogadro's Number}] \times [1/A],$$

where Avogadro's number is $6.022 \times 10^{23}$/mole and A is the atomic mass number of the nuclear species in g/mole.

It must be stressed again that in Equation 1 the density and mass absorption coefficient are those of a specific nuclear isotope only. In the present disclosure, the use of monochromatic photons or a reference scatterer or other scatterer with sufficiently narrow energy resolution that corresponds to the specific isotope under examination serves to assure that a single isotope is evaluated. The isotope has been identified by the energies of the photons that excite the NRF states of that isotope. The nuclear component of the attenuation that is measured is due only to the absorption of the photons by that nuclear isotope. The image of transmission or absorption that is formed is only that of the specific nuclear isotope (designated by the subscript i in Equation 1).

The methods described above permit obtaining data concerning the amount of a specific isotope that is present along any beam path through the target. The NRF detection methods so described may be employed in a system that uses tomographic reconstruction to produce three-dimensional images of the specific isotopes based on their nuclear absorption, and it is this combination of NRF detection and tomographic techniques that is described in detail below. As is set forth more fully below, tomographic techniques may be used with monochromatic or other sufficiently narrow incident beams, and/or with detectors that are sensitive to narrow energy ranges, such as but not limited to reference scatterers made of the same isotope whose presence is being investigated. Tomography also has the advantage that techniques involving measurements at different energies away from the resonant frequencies may not be necessary. That is, if a monochromatic or other sufficiently narrow incident beam is used, or if reference scatterers or other detectors with sufficient energy resolution are used with beams of broad energy content, the isotope being evaluated may be imaged based on the absorption in the target at the resonant energy only.

Figure 1:
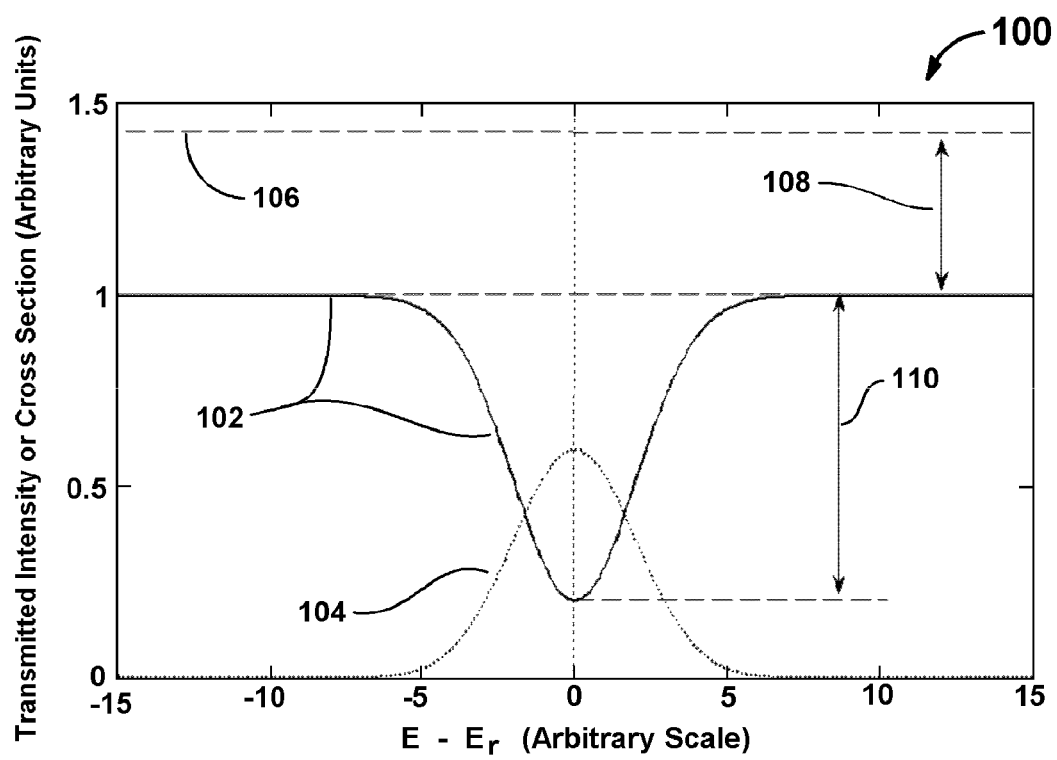
FIG. 1 shows the form of the energy spectrum resulting from the transmission through a target of photons covering a broad energy spectrum. The resonant absorption and electronic absorption are illustrated as well as the use of a reference scatterer for the measurement of NRF absorption.

In the pairs of FIGS. 2A and 2B, 3A and 3B, and 4A and 4B, the identification of the system views as "top" or "side" is arbitrary, and the equipment may be oriented as is convenient. In any event, however, the two views in each pair of figures are intended to be at right angles to each other.

DETAILED DESCRIPTION OF EMBODIMENTS

The embodiments described herein are exemplary of the possible applications of the technology and methods disclosed herein for producing a three-dimensional image of the density of a nuclear isotope in a target by tomographic reconstruction. Those experienced in the art will recognize that there are extensions, modifications and other arrangements of the elements disclosed that can be implemented and those alternative arrangements are intended to be included as part of this disclosure.

In carrying out conventional NRF analysis of a target using reference scatterers as discussed above, or using transmission detectors with sufficiently narrow energy resolution, or using a monochromatic or other sufficiently narrow incident photon beam, if a single photon beam incident direction is used, the result is a two-dimensional image or projection of the target, along the axis of the beam direction.

According to the methods and systems disclosed herein, a two-dimensional projection of the transmitted intensity or the absorption profile can be obtained for many directions through the target or container under examination. The standard algorithms of conventional tomography can be applied to this data and many "slices" generated. The result is a reconstruction of the three-dimensional profile of the density of a specific nuclear isotope in the target or container under examination.

Proceeding in a standard manner, the usual Radon transform well known in the art of conventional computed tomography can be generated for the two-dimension absorption data outlined above for a "slice," in terms of the standard variables r and θ in the case of parallel beam tomography:

$$p(r,\theta) = -\ln(I/I_0),$$

where I and $I_0$ are defined in Equation 1, and $$r = x \cos\theta + y \sin\theta;$$

where r is the value onto which the point (x,y) in the target or sample is projected at an angle θ.

This expression for $p(r,\theta)$ is often written as:

$$p(r, \theta) = \int_0^\infty f(x, y)\delta(x\cos\theta + y\sin\theta - r)dx\,dy,$$

where f(x, y) represents the product of μ and ρ in Equation 1 which (in the case of conventional X-ray tomography) are both functions of x and y, the standard Cartesian coordinates of the material in the target or container under examination. In the case of this disclosure, ρ is a function of x and y but μ is a property of the specific nuclear isotope labeled by the index i in Equation 1 and is determined by the NRF states of that isotope. The inverse Radon transform can be conventionally performed and this generates f(x,y), the two-dimensional distribution of the product of μ and ρ in one "slice" of the target. Once again it is stressed that μ is identified with a specific nuclear isotope by the unique energetic distribution of the NRF lines. These lines are completely known and may be detected when a monochromatic or other sufficiently narrow source is used; these lines also may be determined by use of a reference scatterer when a continuous source is used, or by means of detectors with sufficiently fine energy resolution (such as Ge), whether using a continuous source, a monochromatic or other narrow energy range source, or a source including a plurality of monochromatic lines or narrow energy ranges. Implicit in this discussion is the need to scan a target to produce other "slices" of the material as with conventional X-ray tomography. Thus, the three-dimensional distribution ρ(x,y,z), of the specific nuclear isotope may be determined. The example of parallel beam tomography discussed herein is used for its simplicity of description and is not intended to imply limitation. Those skilled in the art will recognize that the basic principles are the same for different geometrical situations in the scanning of an object and those different geometries are intended as part of the disclosure. For further discussions of the principles of conventional computer aided tomography, other geometries and their applications and advantages see "*Computed Tomography, Physical Principles Clinical Applications and Quality Control*", Euclid Seeram, RT®, BSc, MSC, Medical Imaging, Advanced Studies, British Columbia, Canada; W. B. Saunders Company, a division of Harcourt Brace and Company, Philadelphia, Pa., (1994) and references cited therein.

It should be appreciated that certain of the techniques described hereinbelow will employ measurements at different energies to permit the nuclear part of the absorption coefficient, μ, to be separated from the electronic component. This separation of the nuclear and electronic parts is not necessary to achieve the three dimensional imaging of a specific isotope, however, because the tomographic transforms are sufficiently general to account for the nuclear absorption as long as the signal is not overwhelmed by excessive non resonant photons. Detectors with adequate resolution and/or incident photon energies sufficiently tuned to the resonant absorption lines of a specific isotope are sufficient. As long as the resonant absorption of a specific isotope can be measured by the use of monochromatic or narrow-energy-range incident photons and/or the detection methods can isolate the appropriate photon energies when a continuous incident photon spectrum is used, the tomographic algorithms will yield a three dimensional identification of the specific isotope(s) involved. Certain qualities such as contrast may be affected by not separating the nuclear and electronic components explicitly but the tomographic transformation may still be accomplished.

There are many refinements in the technology for performing the inverse Radon transforms, and there are many geometries used to make the original absorption images which enhance various characteristics of the derived μ(x,y). These are all well known to those versed in the art and they are assumed as part of this disclosure.

For a better understanding of the present disclosure, together with other and further objects thereof, reference is made to the accompanying drawings and the following detailed description.

The process of using a reference scatterer is illustrated in FIG. 1, which shows a graph 100 illustrating the transmitted intensity of photons from a beam transmitted through an absorbing material including a specific nuclear isotope. The energy dependence of the transmission is shown in the vicinity of a nuclear resonance energy $E_r$ for the specific nuclear isotope. The photon beam is made up of photons with continuously distributed energies and has an incident intensity distribution as a function of energy 106 as shown in the graph. The horizontal scale of the graph 100 is in arbitrary units of the difference $E-E_r$, where E is the photon energy and $E_r$ is the energy of the NRF state of the specific nuclear isotope. The absorption of the beam by standard electronic processes, as discussed above and as might previously have been employed for conventional radiography and/or conventional tomographic reconstruction, is shown as electronic absorption 108. The incident energy spectrum 106 of the incident photon beam is shown as flat since the horizontal scale, although arbitrary, is on the order of eV while the incident photon energy is on the order of MeV and is assumed to change slowly over the horizontal scale of eV shown. The transmitted intensity 102 of the incident photon beam shows a flat region in the energies relatively distant from $E_r$, but shows a valley 110 at $E_r$. The nuclear absorption of the specific nuclear isotope due to nuclear resonance causes attenuation in addition to the electronic absorption 108 and this creates the valley 110 in the transmitted intensity 102.

The cross section 104 for NRF scattering by a reference scatterer is also shown in FIG. 1. The reference scatterer is assumed to be of the same nuclear species as the specific nuclear isotope that makes up at least some of the absorbing material in the target through which the photon beam is transmitted. Of course, the absorbing material may consist of other nuclear species in addition to that of the reference scatterer. Those other materials contribute only to the flat electronic attenuation shown in the graph 100, while the specific nuclear isotope that is the same as the reference scatterer provides the valley 110 caused by the nuclear absorption of the NRF state. For convenience herein, we refer to such a valley 110 as a "hole". While the best photon detectors have energy resolutions of ~3 keV at photon energies of a few MeV, the reference scatterer has an energy resolution of only a few eV as determined by the Doppler-broadened NRF state.

When a photon beam relatively broad in energy passes through both an unknown absorbing material and a reference scatterer containing a specified isotope, the presence of a reduction in the intensity of the scattered beam from the reference scatterer at the energy $E_r$, as compared to that which would be expected in the absence of the specified isotope in the unknown absorbing material, or as compared to the intensity of the transmitted beam as detected in a transmission detector with broad energy sensitivity, is indicative that the material in the reference scatterer is also present in the unknown absorbing material. Similarly, when a transmission detector is used with a monochromatic or narrow energy range incident photon beam, and the incident beam energy is varied, a "hole" in the transmitted beam intensity is indicative that the material with an NRF resonance at the "hole" energy is also present in the unknown absorbing material. Similarly, when a transmission detector with sufficiently narrow energy resolution is used with a photon beam relatively broad in energy, a "hole" in the transmitted beam intensity is indicative that the material with an NRF resonance at the "hole" energy is also present in the unknown absorbing material.

Embodiments of the methods and systems disclosed herein may have as part of their implementation some aspect of the systems and geometric arrangements shown schematically in FIGS. 2A, 2B, 3A, 3B, 4A and 4B.

Figure 2A:
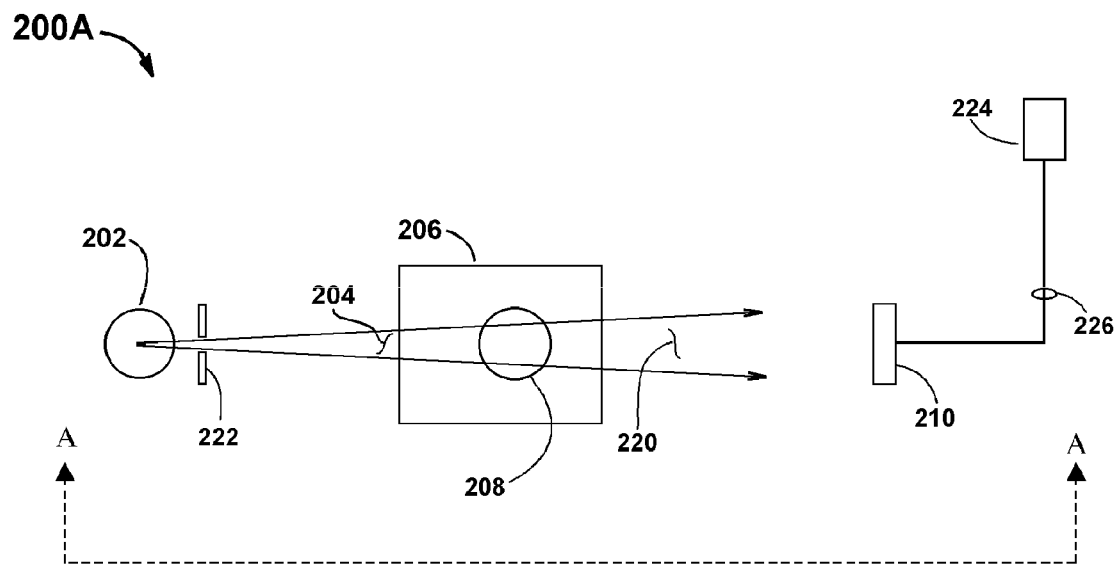
FIG. 2A shows a top view schematic of an exemplary embodiment of a system for computed tomography using NRF absorption.
Figure 2B:
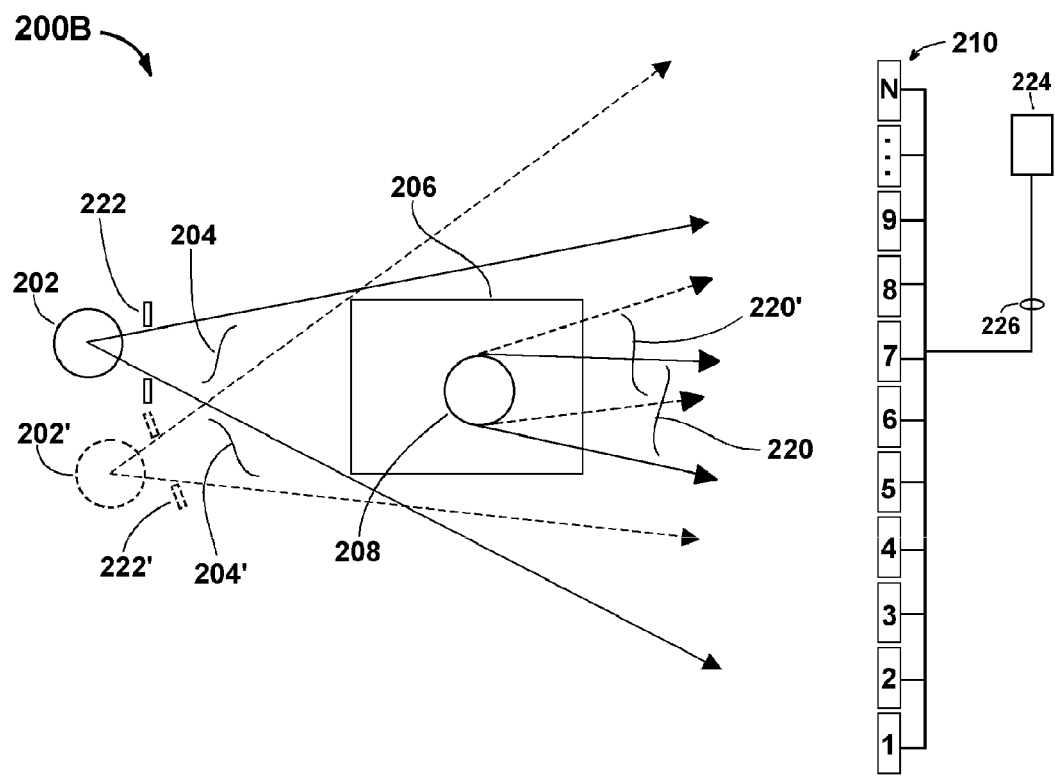
FIG. 2B shows a side sectional view of the system (View A-A in FIG. 2A)

FIG. 2A shows a top view 200A of a system 200. FIG. 2B is a side view 200B of the same system 200 along a direction indicated by a viewing line A-A in FIG. 2A. Views 200A and 200B in FIGS. 2A and 2B, respectively, are different views of the same system 200. (As discussed above, the identification of the views in FIGS. 2A and 2B as "top" and "side" may be interchanged.)

Referring to FIG. 2A, a photon source 202 may be collimated by collimator 222 to form a photon beam 204 that impinges on a container 206 containing a target material 208. Container 206 may contain other materials (not shown). The target material 208 may include a specific nuclear species capable of undergoing NRF resulting from excitation by the photon beam 204. It is desired that the specific nuclear species in the target material 208 within the container 206 be detected and imaged. Some of the photons in the photon beam 204 are absorbed by the target material 208 and some scatter from the target material 208, resulting in attenuated photon beam 220.

The non-resonant scattering processes include Compton scattering, Rayleigh scattering and Delbruck scattering as discussed above. The atomic photoelectric effect and pair-production also contribute to absorption of the beam. The process that is specific to particular nuclear isotopes (and thus to the specific nuclear species desired to be imaged in the target material 208) is Nuclear Resonance Fluorescence (NRF). While the aforementioned non-resonant processes are only slowly energy dependent, the absorption and scattering of photons by the NRF states of a specific nuclear isotope in the target material 208 produces narrow "holes" in the transmitted spectrum of the attenuated photon beam 220 at incident photon energies characteristic of the specific NRF interactions occurring. These "holes" thus identify the nuclear isotope(s) present in the target material.

The attenuated photon beam 220 is incident on a transmission detector array 210. The detector array 210 may for example be a linear array or a curvilinear array of detecting elements, may be sensitive to the photon energy in the attenuated photon beam 220, and may be capable of measuring and transmitting photon count and photon energy signals via electrical or optical leads 226 or wirelessly to a processor 224 that may comprise one or more computers. The processor 224 may record and analyze the nature of the signals according to algorithms developed for the purpose of imaging the material of interest in the target material 208.

The photon source 202 may provide photons continuously distributed in energy such as bremsstrahlung, or it may provide photons limited to an energy range resulting from processes such as nuclear reactions, Compton scattering, and laser backscattering from an electron beam. The photon source 202 may be monochromatic such as those photons produced by laser backscattering and other processes such as neutron capture reactions. For additional information on various possible photon sources see U.S. Patent Application 2006/0188060A1 cited and incorporated by reference above. Monochromatic or narrow-energy-range photon sources, when used as photon source 202, may contain one or several monochromatic photon "lines" or narrow energy ranges but in the embodiments of the methods and systems disclosed herein, one or more of the lines (not necessarily all) may be used. Those skilled in the art will recognize that there are many possibilities for the photon source 202 and they are all intended to be a part of the disclosure. If the photon beam is monochromatic or limited to a narrow range, the energy of the photon beam may be varied in order to compare the transmitted flux at an NRF energy for a specific nuclear isotope with the transmitted flux away from that resonant energy, in order to determine whether that isotope is present in the target material 208 being scanned. Alternatively, a plurality of monochromatic lines or narrow energy ranges may be included in the incident photon beam, and a detector array with sufficiently narrow energy resolution used, to permit the separation of signals resulting from resonant scattering from isotopes with resonances corresponding to the different incident monochromatic energies or energy ranges. In this case, the presence of a "hole" in the transmitted intensity at a given energy as measured in the detector array will be indicative of the presence of a nuclear isotope with an NRF state at the "hole" energy. Alternatively, if the photon beam has a broad energy spectrum but the detector array has sufficiently narrow energy resolution, the presence of a "hole" in the transmitted intensity at a given energy as measured in the detector array again will be indicative of the presence of a nuclear isotope with an NRF state at the "hole" energy. In addition, as described above the presence of the nuclear isotope may be detected using tomographic algorithms based solely on measurements using incident monochromatic photons or incident beams with narrow energy ranges at the resonant energy, or using an incident photon beam with a broad energy spectrum but detectors such as but not limited to reference scatterers with the ability to detect scattering or transmission at the resonant energy.

FIG. 2B is a view 200B of the system 200 along a direction indicated by viewing line A-A in FIG. 2A that may be at right angles to FIG. 2A. Referring to FIG. 2B, transmission detector array 210 comprises multiple detector elements 210-1, 210-2, ... through 210-N, which are indicated by the numbers 1, 2, ... N. All of the detector elements 210-1, 210-2, ... 210-N are connected wirelessly or by electrical or optical leads 226 to the processor 224. The photon source 202 provides the photon beam 204, which is fan-shaped in this view. The fan shape may be provided by the characteristics of the photon source 202. Alternatively, the fan shape may be derived by scanning (not shown) a narrower beam into the fan shape indicated by, e.g., rotating the photon source 202.

Where the photon beam 204 passes through the target material 208 it produces the attenuated photon beam 220. The photon beam 204 and the attenuated photon beam 220 project onto the detector array 210 for imaging a slice of the container 206 and its contents including target material 208. In some embodiments, the photon source 202 may be located in one or more alternate positions, such as indicated, for example and not by way of limitation, by photon source 202' (in dotted lines). Photon source 202' produces photon beam 204' and attenuated photon beam 220'. Photon beam 204' may be collimated with collimator 222'. Photon beam 204' and attenuated photon beam 220' project onto the detector array 210 for alternatively imaging the slice of the container and its contents.

The photon source 202 and optional collimator 222 may be moved to many alternative locations in addition to 202' and 222' (not shown) to allow a tomographic image of one slice to be constructed. The number of locations depends on the spatial resolution and contrast required of the system images. The photon source 202 may be translated in position by one of several methods, some being mechanical as with radioactive material sources or small accelerators, and others being electromagnetic as with sources involving the transport of beams of protons, alpha-particles or electrons. The motion of the source may be in a straight line or it may be along a curved trajectory around the target depending on the details of the geometry that is employed. In other embodiments the source can be stationary and the target and/or detectors moved to accomplish a number of trajectories through the target. In other embodiments, a plurality of stationary and/or mobile sources may be used, rather than a single source which is scanned. Those experienced in the tomographic reconstruction art will recognize that there are many possibilities for locating the source or sources in different positions around the target, and in moving the source or sources, each with its own advantages depending on the nature of the tomographic images that are desired as well as speed and economy of operation. These other possibilities represent modifications of the methods disclosed herein and they are all intended as part of the disclosure. Additional slices may be imaged by translating the container 206 with its target material 208 or the photon source 202 and the detector array 210 in a direction into and/or out of the plane of FIG. 2B. Thus full three-dimensional imaging can be achieved by tomographic reconstruction.

For the system 200 as shown in FIGS. 2A and 2B, the photon source 202 may produce a monochromatic or narrow-energy-range photon beam 204 that may be resonant with the NRF states in the specific nuclear species in the target material 208. When such a photon beam 204 is used the transmission detector array 210 may be an array of simple photon detectors with or without energy resolution. The target material 208 scatters the resonant photons in the photon beam 204 and thus produces an attenuation at the resonant energy that is greater than the attenuation produced solely by electronic absorption of the target material 208 in the container 206 at other energies. By monitoring the electronic absorption level, the nuclear absorption can be determined from the total absorption, and the specific nuclear species in the target material 208 can be imaged. The electronic absorption can be monitored by shifting the energy of the photons in the photon beam 204 to be significantly different than the energy of the NRF state so that NRF absorption is not a significant quantity. Alternatively, in view of the power of the tomographic techniques, all of the measurements may be made at the resonant energy.

In another embodiment, the photon source 202 may have one or more additional monochromatic line(s) or narrow energy ranges that are not resonant with the NRF state of the target material 208. The absorption of these non-resonant photon lines provides a means of monitoring the general electronic absorption. Because the energy or energies of the non-resonant photons is not the same as that of the NRF state in the target material 208, a correction may be applied to correct for the difference in the electronic absorption at the differing energies according to techniques that are well known to those skilled in the art. See, for example, U.S. Pat. No. 7,286,638, Ledoux et al., "Methods And Systems For Determining The Average Atomic Number And Mass Of Materials", and U.S. Pat. No. 7,120,226, Ledoux et al., "Adaptive Scanning Of Materials Using Nuclear Resonance Fluorescence Imaging", both incorporated herein by reference.

In yet another embodiment, the photon source 202 may produce photons with continuously distributed energy as from a bremsstrahlung source. With a photon beam 204 having photons with a continuous energy distribution, the detector array 210 requires detector elements 210-1, 210-2, ... 210-N having a high energy resolution, as for example detector elements based on an array of reference scatterers (further described below), or an array of high resolution germanium detectors. In this case, the presence of a "hole" at a specific energy in the energy spectrum of photons incident on the transmission detectors will reveal the presence of material in the target containing the nuclear isotope having an NRF state at the energy of the "hole."

Figure 3A:
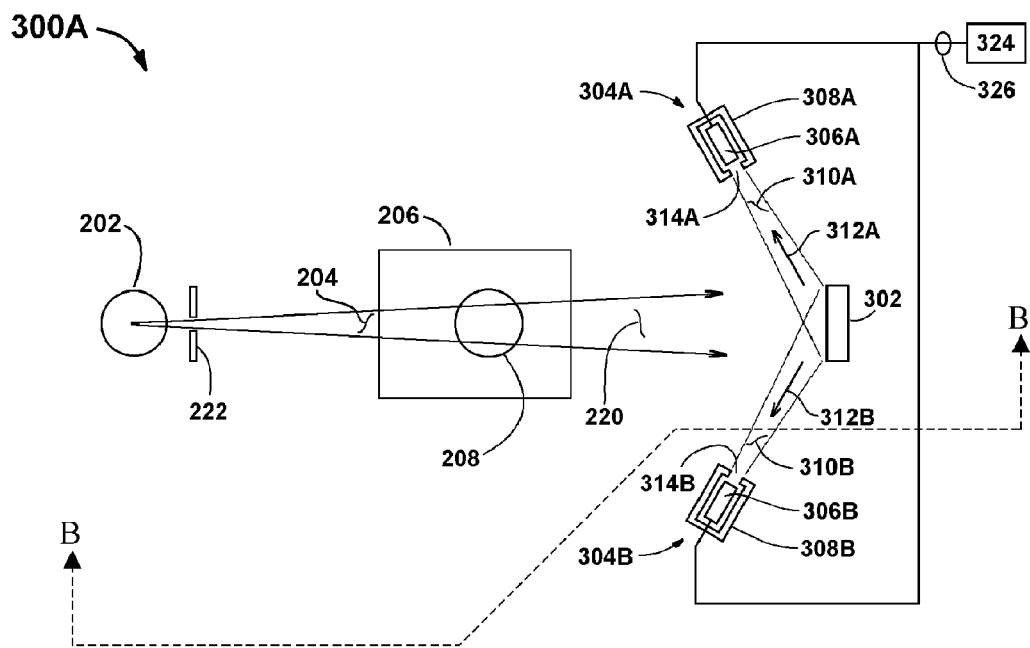
FIG. 3A shows a top view schematic of an alternative exemplary embodiment of a system for computed tomography using NRF absorption with a reference scatterer.
Figure 3B:
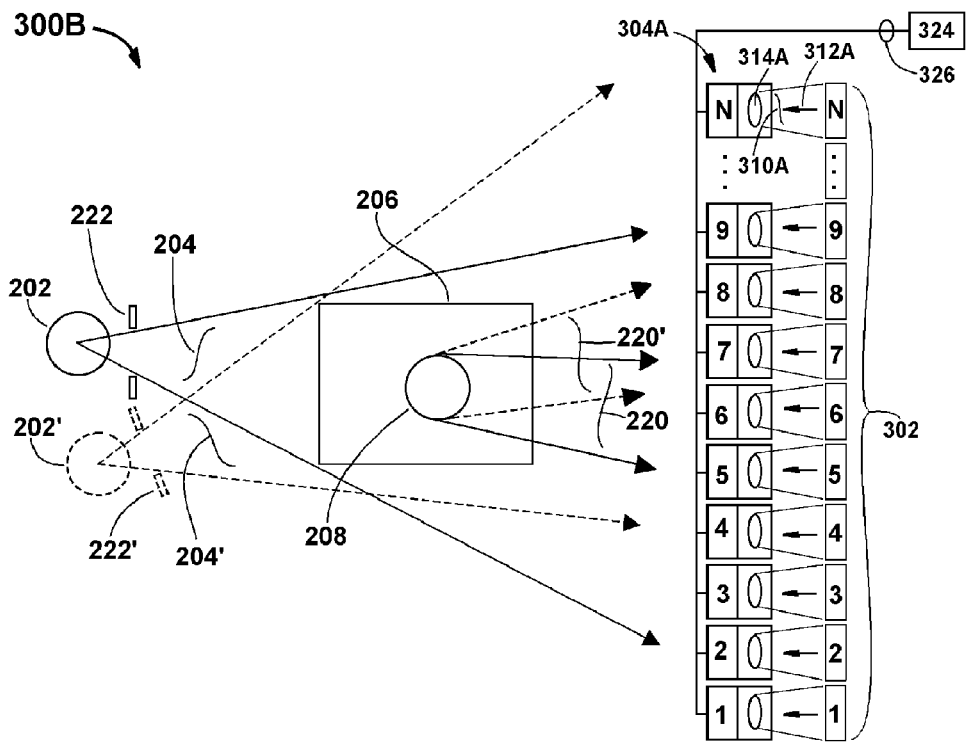
FIG. 3B shows a side sectional view of the system (View B-B in FIG. 3A)

FIG. 3A shows a top view 300A of a system 300. FIG. 3B is a side view 300B of the same system 300 along a direction indicated by viewing line B-B in FIG. 3A. Views 300A and 300B in FIGS. 3A and 3B, respectively, are different views of the same system 300. (As discussed above, the identification of the views in FIGS. 3A and 3B as "top" and "side" may be interchanged.)

In FIGS. 3A and 3B items with like designator numbers to those in FIGS. 2A and 2B are like items and they may be used in like or analogous ways, as will be apparent to the person of skill in the art. The system 300 of FIGS. 3A and 3B differs from the system 200 of FIGS. 2A and 2B in that the attenuated photon beam 220 (220') does not project directly onto a transmission detector array 210 for imaging, but rather projects onto a reference scatterer array 302 such that photons scattered from the reference scatterer array 302 are detected in one or more detector arrays 304A, 304B.

Referring to FIG. 3A, the photon beam 204 may be generated and collimated, and may be attenuated by scattering from the target material 208 in the target container 206 to produce an attenuated photon beam 220, in a fashion similar to that described above with respect to FIGS. 2A and 2B.

The attenuated photon beam 220 then may be incident on a reference scatterer array 302 rather than a detector array 210. The reference scatterer array 302 may for example be a linear array or a curvilinear array of reference scattering elements. The reference scatterer may contain a known nuclear isotope whose presence in the target material it may be desired to image. The reference scatterer array 302 facilitates measuring the attenuation due to the presence of that isotope in the target material 208 when the photons in the attenuated photon beam 220 project onto and are resonantly (NRF) scattered by the reference scatterer array 302 into one or more detector arrays (304A and 304B, for example, and not by way of limitation). The scattered photons (312A and 312B) scattered by the reference scatterer array 302 are detected by the one or more detector arrays 304A, 304B. Detector arrays 304A and 304B each have detector array elements having detectors 306A, 306B and shield/collimators 308A, 308B. Shield/collimators 308A, 308B each have entrance apertures 314A, 314B that provide collimation so that each detector array element of each detector array 304A, 304B has a collimated field of view 310A, 310B of only a single reference scattering element of the reference scatterer array 302. The detectors 306A, 306B may be sensitive to the photon energy of the scattered photons 312A, 312B and may be capable of measuring and transmitting photon count and photon energy signals wirelessly or via electrical or optical leads 326 to a processor 324 that may comprise one or more computers. The processor 324 may record and analyze the nature of the signals according to algorithms developed for the purpose of imaging the material of interest in the target material 208.

The photon source 202 may provide photons continuously distributed in energy such as by bremsstrahlung, or by Compton scattering, or another process. The presence of the target material 208 causes the attenuated photon beam 220 to have "holes" in its energy spectrum due to the absorption and scattering of photons by the NRF states of specific nuclear isotopes in the target material 208. The (non-NRF-resonant) electronic absorption can be determined by observing the absorption of photons near but not identical to the NRF state of the specific nuclear species in the target material 208, as for example by placing transmission detectors (not shown) that have a broad energy sensitivity in the path of the attenuated photon beam after the reference scatterer array 302.

FIG. 3B is a view 300B of the system 300 along viewing line B-B indicated in FIG. 3A that may be at right angles to FIG. 3A. Referring to FIG. 3B, reference scatterer array 302 comprises multiple reference scatterer array elements 302-1, 302-2, . . . 302-N, which are indicated by the numbers 1, 2, . . . N. For each of the reference scatterer array elements 302-1, 302-2, . . . 302-N in the reference scatterer array 302 there is a corresponding detector array element 304A-1, 304A-2, . . . 304A-N of the detector array 304A (also true of any additional detector arrays such as 304B not shown in this view for simplicity). Each of the detector array elements 304A-1, 304A-2, . . . 304A-N has an entrance aperture 314A providing a collimated field of view 310A accepting scattered photons 312A from a single reference scatterer element. Each detector array element 304A-1, 304A-2, . . . 304A-N receives scattered photons 312A from the corresponding reference scatterer array element 302-1, 302-2, . . . 302-N. All of the detector array elements 304A-1, 304A-2, . . . 304A-N are connected wirelessly or by electrical or optical leads 326 to the processor 324. Although not shown in this view, the geometries and electrical connections for any additional detector arrays 304B (FIG. 3A) for example are similar to those shown for detector array 304A.

The presence of the target material 208 causes the attenuated photon beam 220 spectrum to have "holes" at specific energies due to the absorption and scattering of photons by the NRF states of specific nuclear isotopes in the target material 208. Thus, if the reference scatterer contains a nuclear isotope that also was present in the target material, the scattering from that isotope in the reference scatterer will be sensitive to the "hole" at the corresponding energy in the energy spectrum of the photons transmitted through the target. This will result in corresponding decreases in the flux of NRF scattered photons 312A from the reference scatterer elements that receive the photon beam from that location as compared to the flux of NRF scattered photons 312A scattered from reference scatterer array elements which have received projections of the photon beam 204 without the nuclear resonance attenuation of the photon beam 220 due to NRF effects caused by the presence of that isotope in the target material 208. That is, in some orientations of the source 220, photon beam 204 and target material 208 the photons incident on some of the reference scatterers do not pass through portions of the target material 208 containing the nuclear isotope being mapped. This is analogous to regular tomography. The outputs of the detector array elements 304A-1, 304A-2, . . . 304A-N (as well as outputs of any other detector arrays) are analyzed by the processor 324 to generate a full three-dimensional image of the specific nuclear species in the target material 208.

In another embodiment, the reference scatterer array 302 may comprise an array of reference scatterer array elements 302-1, 302-2, . . . 302-N that each comprises more than one reference scattering material. The one or more scattering materials in each reference scatterer array element may be present in the form of a mixture, or in layers, or in another arrangement. When multiple scattering materials are present in each reference scatterer array element, multiple specific nuclear species may be detected and imaged in the target material 208 or in other regions in the container 206.

In another embodiment, the reference scatterer array 302 may comprise an array of reference scatterer array elements 302-1, 302-2, . . . 302-N that each comprise two reference scattering materials—one being the material of the specific nuclear species being mapped in the target material 208, and another with a second reference nuclear species not normally present in the container 206 and having NRF lines that are close in energy to those of the nuclear species being mapped but sufficiently different so that the incident photons at the energies of those lines do not suffer resonant nuclear absorption from the nuclear species being mapped. The second nuclear species can be used to provide electronic absorption monitoring such that the amount of attenuation from the nuclear species being mapped may be determined by comparison. More than one such additional nuclear species can be employed to ensure that no material in the container 206 has NRF lines that would interfere with the monitoring of electronic attenuation.

Referring to FIG. 3B, the photon beam may be provided with a fan shape, the photon source may be moved, and/or multiple photon sources may be used, in order to facilitate tomographic reconstruction, as described above in connection with FIG. 2B.

Figure 4A:
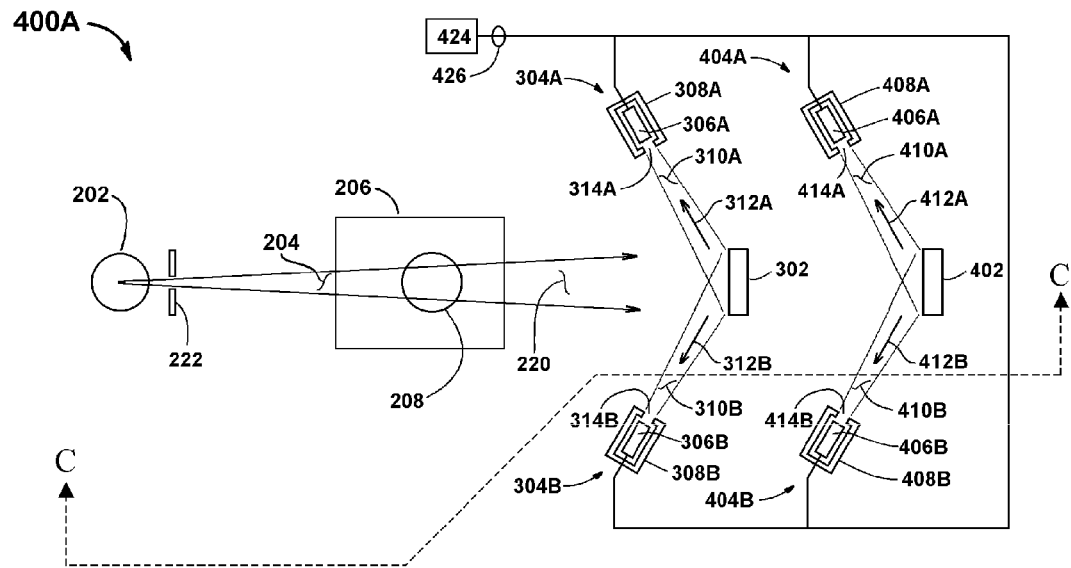
FIG. 4A shows a top view schematic of another alternative exemplary embodiment of a system for computed tomography using NRF absorption with multiple reference scatters.
Figure 4B:
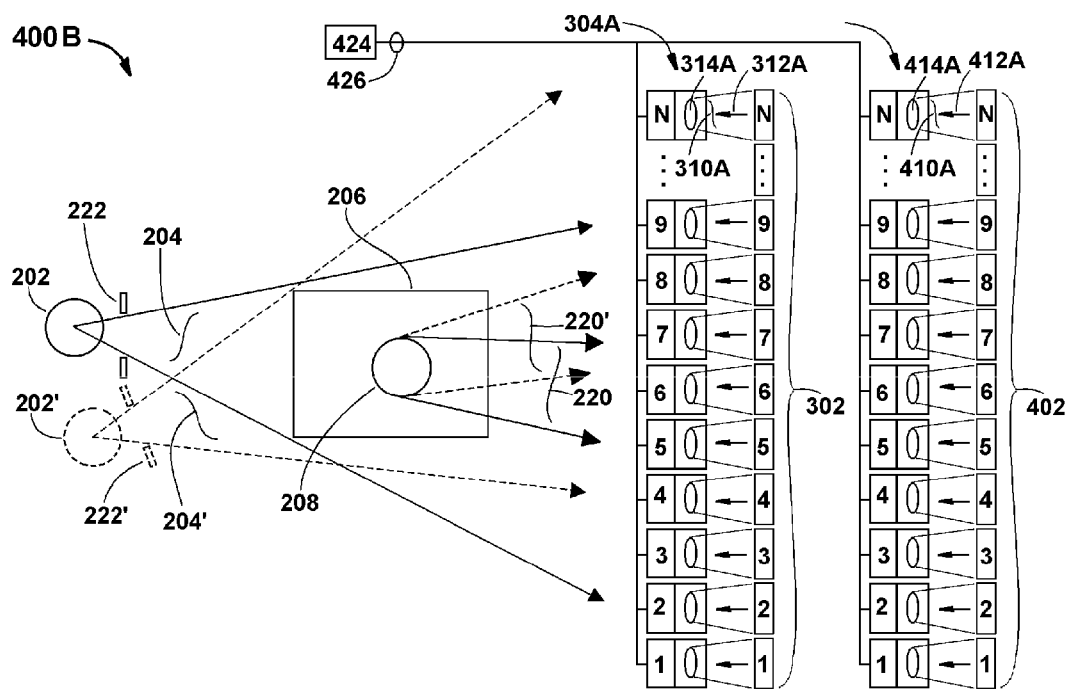
FIG. 4B shows a side sectional view of the system (View C-C in FIG. 4A).

FIG. 4A shows a top view 400A of a system 400. FIG. 4B is a side view 400B of the same system 400 along viewing line C-C in FIG. 4A. Views 400A and 400B in FIGS. 4A and 4B, respectively, are different views of the same system 400. (As discussed above, the identification of the views in FIGS. 4A and 4B as "top" and "side" may be interchanged.)

In FIGS. 4A and 4B items with like designator numbers to those in FIGS. 2A, 2B, 3A and 3B are like items and they may be used in like or analogous ways, as will be apparent to the person of skill in the art. The system 400 of FIGS. 4A and 4B differs from the system 300 of FIGS. 3A and 3B in that the system 400 has multiple reference scatterer arrays with multiple detector arrays separately detecting scattered photons from each of the multiple reference scatterer arrays.

Referring to FIG. 4A, the photon beam 204 may be generated and collimated, and may be attenuated by scattering from the target material 208 in the target container 206 to produce an attenuated photon beam 220, in a fashion similar to that described above with respect to FIGS. 2A and 2B.

The attenuated photon beam 220 then may be incident on a reference scatterer array 302 rather than a detector array 210. It then may pass through reference scatterer array 302 and additionally be incident on one or more additional reference scatterer array(s) 402 (only one is shown for simplicity and clarity). As with the reference scatterer array 302, the reference scatterer array 402 may for example be a linear array or a curvilinear array of reference scattering elements. The reference scatterer array 402 facilitates measuring the attenuation due to an additional specific nuclear species in the target material 208 when the photons in the attenuated photon beam 220 project onto and are resonantly (NRF) scattered by the reference scatterer array 402 into one or more detector arrays (404A and 404B, for examples, not limitation). The scattered photons (412A and 412B) scattered by the reference scatterer array 402 are detected by the one or more detector arrays 404A, 404B. Detector arrays 404A and 404B each have detector array elements having detectors 406A, 406B and shield/collimators 408A, 408B. Shield/collimators 408A, 408B each have entrance apertures 414A, 414B that provide collimation so that each detector array element of each detector array 404A, 404B has a collimated field of view 410A, 410B of only a single reference scattering element of the reference scatterer array 402. The detectors 406A, 406B may be sensitive to the photon energy of the scattered photons 412A, 412B and may be capable of measuring and transmitting photon count and photon energy signals wirelessly or via electrical or optical leads 426 to a processor 424 that may comprise one or more computers. The processor 424 may record and analyze the nature of the signals according to algorithms developed for the purpose of imaging the material of interest in the target material 208.

The photon source 202 may provide photons continuously distributed in energy such as by bremsstrahlung, or by Compton scattering, or another process. The presence of the target material 208 causes the attenuated photon beam 220 to have "holes" in its energy spectrum due to the absorption and scattering of photons by the NRF states of specific nuclear isotopes in the target material 208. The (non-NRF-resonant) electronic absorption can be determined by observing the absorption of photons near but not identical to the NRF state of the specific nuclear species in the target material 208, as discussed above in connection with FIGS. 3A and 3B.

Detector array 304A, 304B may detect a first specific nuclear species present in target material 208 while detector array 404A, 404B may detect a second specific nuclear species present in target material 208. Alternatively, detector array 404A, 404B may be used to detect photons scattered from an NRF state that is close in energy to an NRF state present in the first specific nuclear species present in target material 208, but which is in an isotope believed not to be present, or not likely to be present, in the target material 208. This permits the presence of the first nuclear species in the target to be determined by comparing the signals in the detector array 304A, 304B to the signals in the detector array 404A, 404B which may provide a determination of the electronic absorption by the material 208 in the container 206. In some exemplary situations as discussed above in connection with FIGS. 3A and 3B the resonant scatterers 302 and 402 may contain two or more distinct isotopes each.

FIG. 4B is a view 400B of the system 400 along viewing line C-C indicated in FIG. 4A that may be at right angles to FIG. 4A. Referring to FIG. 4B, reference scatterer array 402 comprises multiple reference scatterer array elements 402-1, 402-2, . . . 402-N, which are indicated by the numbers 1, 2, . . . N. For each of the reference scatterer array elements 402-1, 402-2, . . . 402-N in the reference scatterer array 402 there is a corresponding detector array element 404A-1, 404A-2, . . . 404A-N of the detector array 404A (also true of any additional detector arrays such as 404B not shown in this view for simplicity). Each of the detector array elements 404A-1, 404A-2, . . . 404A-N has an entrance aperture 414A providing a collimated field of view 410A accepting scattered photons 412A from a single reference scatterer element. Each detector array element 404A-1, 404A-2, . . . 404A-N receives scattered photons 412A from the corresponding reference scatterer array element 402-1, 402-2, . . . 402-N. All of the detector array elements 404A-1, 404A-2, . . . 404A-N are connected wirelessly or by electrical or optical leads 426 to the processor 424. Although not shown in this view, the geometries and electrical connections for any additional detector arrays 404B (FIG. 4A) for example are similar to those shown for detector array 404A.

The presence of the target material 208 causes the attenuated photon beam 220 spectrum to have "holes" at specific energies due to the absorption and scattering of photons by the NRF states of specific nuclear isotopes in the target material 208. Thus, if the second reference scatterer contains a nuclear isotope that also was present in the target material, the scattering from that isotope in the second reference scatterer will be sensitive to the "hole" at the corresponding energy in the energy spectrum of the photons transmitted through the target. This will result in corresponding decreases in the flux of NRF scattered photons 412A from the second reference scatterer elements that receive the photon beam from that location as compared to the flux of NRF scattered photons 412A scattered from the second reference scatterer array elements which have received projections of the photon beam 204 without the nuclear resonance attenuation of the photon beam 220 due to NRF effects caused by the presence of that isotope in the target material 208. That is, in some orientations of the source 220, photon beam 204 and target material 208 the photons incident on some of the second reference scatterers do not pass through portions of the target material 208 containing the nuclear isotope being mapped by the second reference scatterer array. This is analogous to regular tomography. The outputs of the detector array elements 404A-1, 404A-2, . . . 404A-N (as well as outputs of any other detector arrays) are analyzed by the processor 424 to generate a full three-dimensional image of the specific nuclear species represented in the second reference scatterer array in the target material 208.

Additional reference scatterer arrays and their corresponding detector arrays may be positioned in tandem with the reference scatterer arrays 302 and 402 to facilitate additional detection and imaging of additional specific nuclear species and/or for monitoring electronic absorption.

Referring to FIG. 4B, the photon beam may be provided with a fan shape, the photon source may be moved, and/or multiple photon sources may be used, in order to facilitate tomographic reconstruction, as described above in connection with FIG. 2B.

In another embodiment compatible with any of the systems 200, 300 and 400, shown in FIGS. 2A through 4B, the general electronic absorption is monitored by standard X-ray detection techniques such as are employed in many applications with X-rays wherein the specific energy of the photons is not monitored. This technique is practical because the nuclear isotopic absorption exists only in the narrow energy region of the NRF state. This region is normally less than a few eV and is unimportant to the total absorption over all photon energies which encompasses the energy scale of MeV and characterizes most continuous sources.

In another embodiment, compatible with any of the systems 200, 300, and 400 shown in FIGS. 2A through 4B, electronic attenuation is used to make a standard tomographic determination of the density distribution in a container 206 along with the isotopic density distribution made using the NRF absorption profile. The added information may be useful to correlate with the isotopic distribution. It is a very penetrating tomography because of the high energy of the photon beam 204 involved. The sum of all NRF images should be the same as the standard X-ray tomography and these data may provide verification and a strong check on the quality of performance.

Although the methods and systems have been described relative to specific embodiments thereof, they are not so limited. Obviously many modifications and variations may become apparent in light of the above teachings.

While the systems and methods disclosed herein have been particularly shown and described with reference to exemplary embodiments thereof, it will be understood by those skilled in the art that various changes in form and details may be made therein without departing from the scope of the disclosure. It should be realized the systems and methods disclosed herein are also capable of a wide variety of further and other embodiments within the spirit of the disclosure. Those skilled in the art will recognize or be able to ascertain using no more than routine experimentation, many equivalents to the exemplary embodiments described specifically herein. Such equivalents are intended to be encompassed in the scope of the present disclosure.

The invention claimed is:

1. A method of determining and displaying three dimensional images of presences of at least one specified nuclear isotope in at least a portion of a target of interest, comprising:
 a) illuminating at least a part of the target with an incident photon beam within a predetermined energy range,
 wherein the incident photon beam comprises photons traveling in at least one first predetermined direction which impinge upon the target at least one first predetermined surface location, and
 wherein the predetermined energy range includes energies at which nuclear resonant fluorescence scattering can take place in each of the at least one specified nuclear isotopes and energies at which it cannot;
 b) detecting in a transmission detector array a plurality of photons from said incident photon beam,
 wherein the transmission detector array is disposed such that at least a portion of said incident photon beam traversing the target is incident on the array, and
 wherein the transmission detector array determines an energy of at least some photons incident on it with accuracy to permit determination of whether the said photon energy corresponds to an energy at which nuclear resonant fluorescence scattering can take place from one of the at least one specified nuclear isotope;
 c) repeating steps a) and b) for a predetermined selection of additional angular directions with respect to the target, and a predetermined selection of surface locations of the target;
 d) based upon numbers of photons detected in the transmission detector array, with energies at which nuclear resonant fluorescence scattering can take place from each of the at least one specified nuclear isotope, determining through use of tomographic computation methods the three dimensional image of the presence of each of the at least one specified nuclear isotope in at least the portion of the target of interest; and
 e) displaying the three dimensional images on an output device to a user.

2. The method of claim 1, wherein the transmission detector array comprises high purity germanium.

3. The method of claim 1, wherein the incident photon beam is a bremsstrahlung beam.

4. The method of claim 1, wherein the incident photon beam is generated by a method chosen from the group consisting of neutron capture, proton capture reactions, laser back scattering and resonant scattering of photons.

5. The method of claim 1, wherein the repetition of steps a) and b) for a predetermined selection of additional directions and surface locations comprises:
 c-1) choosing additional directions and surface locations such that a slice of at least the portion of the target of interest is imaged; and
 c-2) repeating step c-1) for additional slices of the at least the portion of the target of interest.

6. A method of determining and displaying a three dimensional image of a presence of a specified nuclear isotope in at least a portion of a target of interest, comprising:
 a) illuminating at least a part of the target with an incident photon beam within a predetermined energy range,
 wherein the incident photon beam comprises photons traveling in at least one first predetermined direction which impinge upon the target at at least one first predetermined surface location, and
 wherein the predetermined energy range includes energies at which nuclear resonant fluorescence scattering can take place in the specified nuclear isotope and energies at which it cannot;
 b) detecting in a transmission detector array a plurality of photons from said incident photon beam,
 wherein the transmission detector array is disposed such that at least a portion of said incident photon beam traversing the target is incident on the array, and
 wherein the transmission detector array determines an energy of at least some photons incident on it with accuracy to permit determination of whether the said photon energy corresponds to an energy at which nuclear resonant fluorescence scattering can take place from the specified nuclear isotope;
 c) repeating steps a) and b) for a predetermined selection of additional angular directions with respect to the target, and a predetermined selection of surface locations of the target;
 d) based upon numbers of photons detected in the transmission detector array, with energies at which nuclear resonant fluorescence scattering can take place from the specified nuclear isotope, and numbers detected with energies at which nuclear resonant fluorescence scattering cannot take place from the specified nuclear isotope, for a given direction and surface location, determining through use of tomographic computation methods the three dimensional image of the presence of the specified nuclear isotope in at least the portion of the target of interest; and e) displaying the three dimensional image on an output device to a user.

7. The method of claim 6, wherein the transmission detector array comprises high purity germanium.

8. The method of claim 6, wherein the incident photon beam is a bremsstrahlung beam.

9. The method of claim 6, wherein the incident photon beam is generated by a method chosen from the group consisting of neutron capture, proton capture reactions, laser back scattering and resonant scattering of photons.

10. The method of claim 6, wherein the repetition of steps a) and b) for a predetermined selection of additional directions and surface locations comprises:

c-1) choosing additional directions and surface locations such that a slice of at least the portion of the target of interest is imaged; and c-2) repeating step c-1) for additional slices of the at least the portion of the target of interest.

11. The method of claim 6, wherein the predetermined energy range includes energies at which nuclear resonant fluorescence scattering can take place in at least one additional specified nuclear isotope and energies at which it cannot, wherein the transmission detector array determines an energy of at least some photons incident on it with accuracy to permit determination of whether the said photon energy corresponds to an energy at which nuclear resonant fluorescence scattering can take place from the at least one additional specified nuclear isotope; and further comprising, based upon numbers of photons detected in the transmission detector array, with energies at which nuclear resonant fluorescence scattering can take place from the at least one additional specified nuclear isotope, and numbers detected with energies at which nuclear resonant fluorescence scattering cannot take place from the at least one additional specified nuclear isotope, for a given direction and surface location, determining through use of tomographic computation methods three dimensional images of the presence of each of the at least one additional specified nuclear isotope in at least the portion of the target of interest; and further comprising, displaying the three dimensional images on an output device to a user.

12. A method of determining and displaying a three dimensional image of a presence of a specified nuclear isotope in at least a portion of a target of interest, comprising:

a) illuminating at least a part of the target with an incident photon beam within a predetermined energy range, wherein the incident photon beam comprises photons traveling in at least one first predetermined direction which impinge upon the target at at least one first predetermined surface location, and wherein the predetermined energy range includes energies at which nuclear resonant fluorescence scattering can take place in the specified nuclear isotope and energies at which it cannot;

b) detecting in at least one detector array a plurality of photons produced by nuclear resonance fluorescence in a first reference scatterer array;

wherein the first reference scatterer array comprises the specified nuclear isotope, wherein the first reference scatterer array is disposed such that at least a portion of said incident photon beam traversing the target is incident on the array, and wherein the detector array is disposed such that at least some photons scattered from the first reference scatterer array by nuclear resonance fluorescence are incident on the detector array;

c) repeating steps a) and b) for a predetermined selection of additional angular directions with respect to the target, and a predetermined selection of surface locations of the target;

d) based upon numbers of photons detected in the detector array, for a given direction and surface location, determining through use of tomographic computation methods the three dimensional image of the presence of the specified nuclear isotope in at least the portion of the target of interest; and e) displaying the three dimensional image on an output device to a user.

13. The method of claim 12, wherein the incident photon beam is a bremsstrahlung beam.

14. The method of claim 12, wherein the incident photon beam is generated by a method chosen from the group consisting of neutron capture, proton capture reactions, laser back scattering and resonant scattering of photons.

15. The method of claim 12, wherein the repetition of steps a) and b) for a predetermined selection of additional directions and surface locations comprises:

c-1) choosing additional directions and surface locations such that a slice of at least the portion of the target of interest is imaged; and c-2) repeating step c-1) for additional slices of the at least the portion of the target of interest.

16. The method of claim 12, wherein the predetermined energy range includes energies at which nuclear resonant fluorescence scattering can take place in at least one additional specified nuclear isotope and energies at which it cannot, and further comprising:

b-1) detecting in at least one additional detector array a plurality of photons produced by nuclear resonance fluorescence in at least one additional reference scatterer array;

wherein each additional reference scatterer array comprises one of the at least one additional specified nuclear isotopes, wherein each additional reference scatterer array is disposed such that at least a portion of said incident photon beam traversing the target and impinging upon and traversing the first reference scatterer array is incident on the array, and wherein each of the at least one additional detector arrays is disposed such that at least some photons scattered from one of the additional reference scatterer arrays by nuclear resonance fluorescence are incident on the detector array;

c-1) repeating step b-1) for a predetermined selection of additional directions and surface locations;

d-1) for each additional detector array, based upon numbers of photons detected in each said array, for a given direction and surface location, determining through use of tomographic computation methods a three dimensional image of the presence of one of the additional specified nuclear isotopes in at least the portion of the target of interest; and e-1) displaying the three dimensional images on an output device to a user.

17. A method of determining and displaying a three dimensional image of a presence of a specified nuclear isotope in at least a portion of a target of interest, comprising:
- a) illuminating at least a part of the target with an incident photon beam within a predetermined energy range,
- wherein the incident photon beam comprises photons traveling in at least one first predetermined direction which impinge upon the target at at least one first predetermined surface location, and
- wherein the predetermined energy range includes energies at which nuclear resonant fluorescence scattering can take place in the specified nuclear isotope and energies at which it cannot;
- b) detecting in at least one detector array a plurality of photons produced by nuclear resonance fluorescence in a reference scatterer array;
- wherein the reference scatterer array comprises the specified nuclear isotope,
- wherein the reference scatterer array is disposed such that at least a portion of said incident photon beam traversing the target is incident on the array, and
- wherein the detector array is disposed such that at least some photons scattered from the reference scatterer array by nuclear resonance fluorescence are incident on the detector array;
- c) detecting in a transmission detector array a plurality of photons from said incident photon beam,
- wherein the transmission detector array is disposed such that at least a portion of said incident photon beam traversing the target and impinging upon and traversing the reference scatterer array is incident on the transmission detector array;
- d) repeating steps a), b) and c) for a predetermined selection of additional angular directions with respect to the target, and a predetermined selection of surface locations of the target;
- e) based upon numbers of photons detected in the detector array, and the transmission detector array, for a given direction and surface location, determining through use of tomographic computation methods the three dimensional image of the presence of the specified nuclear isotope in at least the portion of the target of interest; and
- f) displaying the three dimensional image on an output device to a user.

18. The method of claim 17, wherein the incident photon beam is a bremsstrahlung beam.

19. The method of claim 17, wherein the incident photon beam is generated by a method chosen from the group consisting of neutron capture, proton capture reactions, laser back scattering and resonant scattering of photons.

20. The method of claim 17, wherein the repetition of steps a), b) and c) for a predetermined selection of additional directions and surface locations comprises:
- d-1) choosing additional directions and surface locations such that a slice of at least the portion of the target of interest is imaged; and
- d-2) repeating step d-1) for additional slices of the at least the portion of the target of interest.

21. A method of determining and displaying three dimensional images of presences of at least one specified nuclear isotope in at least a portion of a target of interest, comprising:
- a) illuminating at least a part of the target with an incident photon beam within a predetermined energy range,
- wherein the incident photon beam comprises photons traveling in at least one first predetermined direction which impinge upon the target at at least one first predetermined surface location, and
- wherein the predetermined energy range includes energies at which nuclear resonant fluorescence scattering can take place in each of the at least one specified nuclear isotopes and energies at which it cannot;
- b) detecting in at least one detector array a plurality of photons produced by nuclear resonance fluorescence in a reference scatterer array;
- wherein the reference scatterer array comprises each of the at least one specified nuclear isotopes,
- wherein the reference scatterer array is disposed such that at least a portion of said incident photon beam traversing the target is incident on the array, and
- wherein the detector array is disposed such that at least some photons scattered from the reference scatterer array by nuclear resonance fluorescence are incident on the detector array;
- wherein the detector array determines an energy of at least some photons incident on it with accuracy to permit determination of whether the said photon energy corresponds to an energy at which nuclear resonant fluorescence scattering can take place from one of the at least one specified nuclear isotope;
- c) repeating steps a) and b) for a predetermined selection of additional angular directions with respect to the target, and a predetermined selection of surface locations of the target;
- d) based upon numbers and energies of photons detected in the detector array, for a given direction and surface location, determining through use of tomographic computation methods the three dimensional images of the presence of each of the at least one specified nuclear isotope in at least the portion of the target of interest; and
- e) displaying the three dimensional images on an output device to a user.

22. The method of claim 21, wherein the incident photon beam is a bremsstrahlung beam.

23. The method of claim 21, wherein the incident photon beam is generated by a method chosen from the group consisting of neutron capture, proton capture reactions, laser back scattering and resonant scattering of photons.

24. The method of claim 21, wherein the repetition of steps a) and b) for a predetermined selection of additional directions and surface locations comprises:
- c-1) choosing additional directions and surface locations such that a slice of at least the portion of the target of interest is imaged; and
- c-2) repeating step c-1) for additional slices of the at least the portion of the target of interest.

25. A method of determining and displaying a three dimensional image of a presence of a first specified nuclear isotope in at least a portion of a target of interest, comprising:
- a) illuminating at least a part of the target with an incident photon beam within a predetermined energy range,
- wherein the incident photon beam comprises photons traveling in at least one first predetermined direction which impinge upon the target at at least one first predetermined surface location, and
- wherein the predetermined energy range includes energies at which nuclear resonant fluorescence scattering can take place in the first specified nuclear isotope and energies at which it cannot;
- b) detecting in at least one primary detector array a plurality of photons produced by nuclear resonance fluorescence in a first reference scatterer array;
- wherein the first reference scatterer array comprises the specified first nuclear isotope, wherein the first reference scatterer array is disposed such that at least a portion of said incident photon beam traversing the target is incident on the first array, and wherein the primary detector array is disposed such that at least some photons scattered from the first reference scatterer array by nuclear resonance fluorescence are incident on the primary detector array;

c) detecting in at least one secondary detector array a plurality of photons produced by nuclear resonance fluorescence in a second reference scatterer array;

wherein the second reference scatterer array comprises a specified second nuclear isotope, wherein nuclear resonant fluorescence scattering can take place in the second nuclear isotope with photons at energies in the predetermined energy range, wherein the specified second nuclear isotope is not present in the target in a substantial amount, or the quantity and distribution of the specified second nuclear isotope in the target is known, wherein the second reference scatterer array is disposed such that at least a portion of said incident photon beam traversing the target, and impinging upon and traversing the first reference scatterer array, is incident on the second array, and wherein the secondary detector array is disposed such that at least some photons scattered from the secondary reference scatterer array by nuclear resonance fluorescence are incident on the secondary detector array;

d) repeating steps a), b) and c) for a predetermined selection of additional angular directions with respect to the target, and a predetermined selection of surface locations of the target;

e) based upon numbers of photons detected in the primary detector array and the secondary detector array, for a given direction and surface location, determining through use of tomographic computation methods the three dimensional image of the presence of the first specified nuclear isotope in at least the portion of the target of interest; and f) displaying the three dimensional image on an output device to a user.

26. The method of claim 25, wherein the incident photon beam is a bremsstrahlung beam.

27. The method of claim 25, wherein the incident photon beam is generated by a method chosen from the group consisting of neutron capture, proton capture reactions, laser back scattering and resonant scattering of photons.

28. The method of claim 25, wherein the repetition of steps a), b) and c) for a predetermined selection of additional directions and surface locations comprises:
  d-1) choosing additional directions and surface locations such that a slice of at least the portion of the target of interest is imaged; and
  d-2) repeating step d-1) for additional slices of the at least the portion of the target of interest.

29. A method of determining and displaying a three dimensional image of a presence of a specified nuclear isotope in at least a portion of a target of interest, comprising:
  a) illuminating at least a part of the target with an incident photon beam within a predetermined energy range,
  wherein the incident photon beam comprises photons traveling in at least one first predetermined direction which impinge upon the target at at least one first predetermined surface location, and
  wherein the predetermined energy range comprises energies at which nuclear resonant fluorescence scattering can take place in the specified nuclear isotope;

b) detecting in a transmission detector array a plurality of photons from said incident photon beam,
  wherein the transmission detector array is disposed such that at least a portion of said incident photon beam traversing the target is incident on the array;
  c) repeating steps a) and b) for a predetermined selection of additional angular directions with respect to the target, and a predetermined selection of surface locations of the target;
  d) based upon numbers of photons detected in the transmission detector array, for a given direction and surface location, determining through use of tomographic computation methods the three dimensional image of the presence of the specified nuclear isotope in at least the portion of the target of interest; and
  e) displaying the three dimensional image on an output device to a user.

30. The method of claim 29, wherein the incident photon beam is generated by a method chosen from the group consisting of neutron capture, proton capture reactions, laser back scattering and resonant scattering of photons.

31. The method of claim 29, wherein the repetition of steps a) and b) for a predetermined selection of additional directions and surface locations comprises:
  c-1) choosing additional directions and surface locations such that a slice of at least the portion of the target of interest is imaged; and
  c-2) repeating step c-1) for additional slices of the at least the portion of the target of interest.

32. The method of claim 29, wherein the predetermined energy range is limited to energies at which nuclear resonant fluorescence scattering can take place in the specified nuclear isotope.

33. A method of determining and displaying a three dimensional image of a presence of a specified nuclear isotope in at least a portion of a target of interest, comprising:
  a) illuminating at least a part of the target with an incident photon beam within a first predetermined energy range,
  wherein the incident photon beam comprises photons traveling in at least one first predetermined direction which impinge upon the target at at least one first predetermined surface location, and
  wherein the first predetermined energy range comprises energies at which nuclear resonant fluorescence scattering can take place in the specified nuclear isotope;
  b) detecting in a transmission detector array a plurality of photons from said incident photon beam,
  wherein the transmission detector array is disposed such that at least a portion of said incident photon beam traversing the target is incident on the array;
  c) repeating steps a) and b) for a predetermined selection of additional angular directions with respect to the target, and a predetermined selection of surface locations of the target;
  d) repeating steps a), b) and c) for a second predetermined energy range, wherein the second predetermined energy range is limited to energies at which nuclear resonant fluorescence scattering cannot take place in the specified nuclear isotope;
  e) based upon numbers of photons detected in the transmission detector array, when photons of the first energy range were used, and numbers detected when photons of the second energy range were used, for a given direction and surface location, determining through use of tomographic computation methods the three dimensional image of the presence of the specified nuclear isotope in at least the portion of the target of interest; and f) displaying the three dimensional image on an output device to a user.

34. The method of claim 33, wherein the incident photon beam within the first predetermined energy range is generated by a method chosen from the group consisting of neutron capture, proton capture reactions, laser back scattering and resonant scattering of photons.

35. The method of claim 33, wherein the repetition of steps a) and b) for a predetermined selection of additional directions and surface locations comprises:
   c-1) choosing additional directions and surface locations such that a slice of at least the portion of the target of interest is imaged; and
   c-2) repeating step c-1) for additional slices of the at least the portion of the target of interest.

36. The method of claim 33, wherein the first predetermined energy range is limited to energies at which nuclear resonant fluorescence scattering can take place in the specified nuclear isotope.

37. A method of determining and displaying three dimensional images of presences of a plurality of specified nuclear isotopes in at least a portion of a target of interest, comprising:
   a) illuminating at least a part of the target with an incident photon beam comprising photons within at least two predetermined energy ranges,
   wherein the incident photon beam comprises photons traveling in at least one first predetermined direction which impinge upon the target at at least one first predetermined surface location,
   wherein each predetermined energy range comprises energies at which nuclear resonant fluorescence scattering can take place in one of the plurality of specified nuclear isotopes,
   b) detecting in a transmission detector array a plurality of photons from said incident photon beam,
   wherein the transmission detector array is disposed such that at least a portion of said incident photon beam traversing the target is incident on the array, and
   wherein the transmission detector array determines an energy of at least some photons incident on it with accuracy to permit determination of whether the said photon energy corresponds to an energy at which nuclear resonant fluorescence scattering can take place from one of the plurality of specified nuclear isotopes;
   c) repeating steps a) and b) for a predetermined selection of additional angular directions with respect to the target, and a predetermined selection of surface locations of the target;
   d) based upon numbers of photons detected in the transmission detector array, with energies at which nuclear resonant fluorescence scattering can take place from each of the plurality of specified nuclear isotopes, for a given direction and surface location, determining through use of tomographic computation methods the three dimensional images of the presence of each of the plurality of specified nuclear isotopes in at least the portion of the target of interest; and
   e) displaying the three dimensional images on an output device to a user.

38. The method of claim 37, wherein the incident photon beam within the first predetermined energy range is generated by a method chosen from the group consisting of neutron capture, proton capture reactions, laser back scattering and resonant scattering of photons.

39. The method of claim 37, wherein the transmission detector array comprises high purity germanium.

40. The method of claim 37, wherein the repetition of steps a) and b) for a predetermined selection of additional directions and surface locations comprises:
   c-1) choosing additional directions and surface locations such that a slice of at least the portion of the target of interest is imaged; and
   c-2) repeating step c-1) for additional slices of the at least the portion of the target of interest.

41. A method of determining and displaying a three dimensional image of a presence of a specified nuclear isotope in at least a portion of a target of interest, comprising:
   a) illuminating at least a part of the target with an incident photon beam comprising photons within a first predetermined energy range and photons within a second predetermined energy range,
   wherein the incident photon beam comprises photons traveling in at least one first predetermined direction which impinge upon the target at at least one first predetermined surface location,
   wherein the first predetermined energy range comprises energies at which nuclear resonant fluorescence scattering can take place in the specified nuclear isotope, and
   wherein the second predetermined energy range is limited to energies at which nuclear resonant fluorescence scattering cannot take place in the specified nuclear isotope;
   b) detecting in a transmission detector array a plurality of photons from said incident photon beam,
   wherein the transmission detector array is disposed such that at least a portion of said incident photon beam traversing the target is incident on the array, and
   wherein the transmission detector array determines an energy of at least some photons incident on it with accuracy to permit determination of whether the said photon energy corresponds to an energy at which nuclear resonant fluorescence scattering can take place from the specified nuclear isotope;
   c) repeating steps a) and b) for a predetermined selection of additional angular directions with respect to the target, and a predetermined selection of surface locations of the target;
   d) based upon numbers of photons detected in the transmission detector array, with energies at which nuclear resonant fluorescence scattering can take place from the specified nuclear isotope, and numbers detected with energies at which nuclear resonant fluorescence scattering cannot take place from the specified nuclear isotope, for a given direction and surface location, determining through use of tomographic computation methods the three dimensional image of the presence of the specified nuclear isotope in at least the portion of the target of interest; and
   e) displaying the three dimensional image on an output device to a user.

42. The method of claim 41, wherein the incident photon beam within the first predetermined energy range is generated by a method chosen from the group consisting of neutron capture, proton capture reactions, laser back scattering and resonant scattering of photons.

43. The method of claim 41, wherein the transmission detector array comprises high purity germanium.

44. The method of claim 41, wherein the repetition of steps a) and b) for a predetermined selection of additional directions and surface locations comprises:
   c-1) choosing additional directions and surface locations such that a slice of at least the portion of the target of interest is imaged; and c-2) repeating step c-1) for additional slices of the at least the portion of the target of interest.

45. The method of claim 41, wherein the first predetermined energy range is limited to energies at which nuclear resonant fluorescence scattering can take place in the specified nuclear isotope.

46. A method of determining and displaying a three dimensional image of a presence of a specified nuclear isotope in at least a portion of a target of interest, comprising:
   a) illuminating at least a part of the target with an incident photon beam comprising photons within a first predetermined energy range,
   wherein the incident photon beam comprises photons traveling in at least one first predetermined direction which impinge upon the target at at least one first predetermined surface location, and
   wherein said first predetermined energy range corresponds to energies at which nuclear resonant fluorescence scattering can take place in the specified nuclear isotope;
   b) detecting in at least one detector array a plurality of photons produced by nuclear resonance fluorescence in a reference scatterer array;
   wherein the reference scatterer array comprises the specified nuclear isotope,
   wherein the reference scatterer array is disposed such that at least a portion of said incident photon beam traversing the target is incident on the array, and
   wherein the detector array is disposed such that at least some photons scattered from the reference scatterer array by nuclear resonance fluorescence are incident on the detector array;
   c) repeating steps a) and b) for a predetermined selection of additional angular directions with respect to the target, and a predetermined selection of surface locations of the target;
   d) based upon numbers of photons detected in the detector array, for a given direction and surface location, determining through use of tomographic computation methods three dimensional image of the presence of the specified nuclear isotope in at least the portion of the target of interest; and
   e) displaying the three dimensional image on an output device to a user.

47. The method of claim 46, wherein the incident photon beam in the first predetermined energy range is generated by a method chosen from the group consisting of neutron capture, proton capture reactions, laser back scattering and resonant scattering of photons.

48. The method of claim 46, further comprising repeating steps a), b) and c) for at least one additional predetermined energy range, wherein each additional predetermined energy range comprises energies at which nuclear resonance fluorescence scattering can take place in an additional specified nuclear isotope,
   wherein each said additional photon energy range comprises energies at which nuclear resonance fluorescence scattering can take place in an additional specified nuclear isotope, and
   wherein the reference scatterer further comprises each said additional specified nuclear isotope, and
   further comprising, based upon numbers of photons detected in the detector array, for a given direction and surface location, for each additional predetermined energy range determining through use of tomographic computation methods a three dimensional image of the presence of one of the additional specified nuclear isotopes in at least the portion of the target of interest; and
   further comprising, displaying the said three dimensional images on an output device to a user.

49. A method of determining and displaying a three dimensional image of a presence of a specified nuclear isotope in at least a portion of a target of interest, comprising:
   a) illuminating at least a part of the target with an incident photon beam comprising photons within a predetermined energy range,
   wherein the incident photon beam comprises photons traveling in at least one first predetermined direction which impinge upon the target at at least one first predetermined surface location, and
   wherein said predetermined energy range comprises energies at which nuclear resonant fluorescence scattering can take place in the specified nuclear isotope;
   b) detecting in at least one detector array a plurality of photons produced by nuclear resonance fluorescence in a reference scatterer array;
   wherein the reference scatterer array comprises the specified nuclear isotope,
   wherein the reference scatterer array is disposed such that at least a portion of said incident photon beam traversing the target is incident on the array,
   wherein the detector array determines an energy of at least some photons incident on it with accuracy to permit determination of whether the said photon energy corresponds to an energy at which nuclear resonant fluorescence scattering can take place from the specified nuclear isotope; and
   wherein the detector array is disposed such that at least some photons scattered from the reference scatterer array by nuclear resonance fluorescence are incident on the detector array;
   c) repeating steps a) and b) for a predetermined selection of additional angular directions with respect to the target, and a predetermined selection of surface locations of the target;
   d) based upon numbers and energies of photons detected in the detector array, for a given direction and surface location, determining through use of tomographic computation methods a three dimensional image of the presence of the specified nuclear isotope in at least the portion of the target of interest; and
   e) displaying the three dimensional image on an output device to a user.

50. The method of claim 49, wherein the incident photon beam within each predetermined energy range is generated by a method chosen from the group consisting of neutron capture, proton capture reactions, laser back scattering and resonant scattering of photons.

51. The method of claim 49, wherein the detector array comprises high purity germanium.

52. The method of claim 49, wherein the predetermined energy range is limited to energies at which nuclear resonant fluorescence scattering can take place in the specified nuclear isotope.

53. The method of claim 49, wherein the incident photon beam further comprises photons within at least one additional predetermined energy range,
   wherein each said additional predetermined energy range comprises energies at which nuclear resonance fluorescence scattering can take place in one of the at least one additional specified nuclear isotopes,
   wherein the reference scatterer further comprises each said additional specified nuclear isotope, and
   further comprising, based upon numbers and energies of photons detected in the detector array, for a given direction and surface location, determining through use of tomographic computation methods three dimensional images of the presence of each of the additional specified nuclear isotopes in at least the portion of the target of interest; and further comprising, displaying the said three dimensional images on an output device to a user.

54. A method of determining and displaying a three dimensional image of a presence of a first specified nuclear isotope in at least a portion of a target of interest, comprising:
   a) illuminating at least a part of the target with an incident photon beam comprising photons within a first predetermined energy range and photons within a second predetermined energy range,
   wherein the incident photon beam comprises photons traveling in at least one first predetermined direction which impinge upon the target at at least one first predetermined surface location,
   wherein the first predetermined energy range comprises energies at which nuclear resonant fluorescence scattering can take place in the first specified nuclear isotope,
   wherein the second predetermined energy range is limited to energies at which nuclear resonant fluorescence scattering cannot take place in the first specified nuclear isotope and comprises energies at which nuclear resonant fluorescence scattering can take place in a second specified nuclear isotope, and
   wherein the specified second nuclear isotope is not present in the target in a substantial amount, or the quantity and distribution of the specified second nuclear isotope in the target is known;
   b) detecting in at least one primary detector array a plurality of photons produced by nuclear resonance fluorescence in a first reference scatterer array;
   wherein the first reference scatterer array comprises at least some of the specified first nuclear isotope,
   wherein the first reference scatterer array is disposed such that at least a portion of said incident photon beam traversing the target is incident on the first array, and
   wherein the primary detector array is disposed such that at least some photons scattered from the first reference scatterer array by nuclear resonance fluorescence are incident on the primary detector array;
   c) detecting in at least one secondary detector array a plurality of photons produced by nuclear resonance fluorescence in a second reference scatterer array;
   wherein the second reference scatterer array comprises the specified second nuclear isotope,
   wherein the second reference scatterer array is disposed such that at least a portion of said incident photon beam traversing the target and impinging upon and traversing the first reference scatterer array is incident on the second array, and
   wherein the secondary detector array is disposed such that at least some photons scattered from the secondary reference scatterer array by nuclear resonance fluorescence are incident on the secondary detector array;
   d) repeating steps a), b) and c) for a predetermined selection of additional angular directions with respect to the target, and a predetermined selection of surface locations of the target;
   e) based upon numbers of photons detected in the primary detector array and the secondary detector array, for a given direction and surface location, determining through use of tomographic computation methods the three dimensional image of the presence of the first specified nuclear isotope in at least the portion of the target of interest; and
   f) displaying the three dimensional image on an output device to a user.

55. The method of claim 54, wherein the incident photon beam within the first predetermined energy range is generated by a method chosen from the group consisting of neutron capture, proton capture reactions, laser back scattering and resonant scattering of photons.

56. The method of claim 54, wherein the repetition of steps a), b) and c) for a predetermined selection of additional directions and surface locations comprises:
   d-1) choosing additional directions and surface locations such that a slice of at least the portion of the target of interest is imaged; and
   d-2) repeating step d-1) for additional slices of the at least the portion of the target of interest.

57. The method of claim 54, wherein the first predetermined energy range is limited to energies at which nuclear resonant fluorescence scattering can take place in the first specified nuclear isotope.

58. A method of determining and displaying a three dimensional image of a presence of a specified nuclear isotope in at least a portion of a target of interest, comprising:
   a) illuminating at least a part of the target with an incident photon beam comprising photons within a predetermined energy range,
   wherein the incident photon beam comprises photons traveling in at least one first predetermined direction which impinge upon the target at at least one first predetermined surface location, and
   wherein said predetermined energy range comprises energies at which nuclear resonant fluorescence scattering can take place in the specified nuclear isotope;
   b) detecting in at least one detector array a plurality of photons produced by nuclear resonance fluorescence in a reference scatterer array;
   wherein the reference scatterer array comprises the specified nuclear isotope,
   wherein the reference scatterer array is disposed such that at least a portion of said incident photon beam traversing the target is incident on the array, and
   wherein the detector array is disposed such that at least some photons scattered from the reference scatterer array by nuclear resonance fluorescence are incident on the detector array;
   c) detecting in a transmission detector array a plurality of photons from said incident photon beam,
   wherein the transmission detector array is disposed such that at least a portion of said incident photon beam traversing the target and impinging upon and traversing the reference scatterer array is incident on the transmission detector array;
   d) repeating steps a), b) and c) for a predetermined selection of additional angular directions with respect to the target, and a predetermined selection of surface locations of the target;
   e) based upon numbers of photons detected in the detector array, and the transmission detector array, for a given direction and surface location, determining through use of tomographic computation methods the three dimensional image of the presence of the specified nuclear isotope in at least the portion of the target of interest; and
   f) displaying the three dimensional image on an output device to a user.

59. The method of claim 58, wherein the incident photon beam within each predetermined energy range is generated by a method chosen from the group consisting of neutron capture, proton capture reactions, laser back scattering and resonant scattering of photons.

60. The method of claim 58, wherein the predetermined energy range is limited to energies at which nuclear resonant fluorescence scattering can take place in the specified nuclear isotope.

* * * * *

UNITED STATES PATENT AND TRADEMARK OFFICE
CERTIFICATE OF CORRECTION

| | | |
|---|---|---|
| PATENT NO. | : 8,180,019 B2 | Page 1 of 1 |
| APPLICATION NO. | : 12/958006 | |
| DATED | : May 15, 2012 | |
| INVENTOR(S) | : William Bertozzi et al. | |

It is certified that error appears in the above-identified patent and that said Letters Patent is hereby corrected as shown below:

Title Page, Item (63) (line 1) should read

(63) Continuation-in-part of application No. 11/511,182,

Signed and Sealed this
Tenth Day of July, 2012

David J. Kappos
*Director of the United States Patent and Trademark Office*